(12) United States Patent  (10) Patent No.: US 8,221,353 B2
Cormier et al.  (45) Date of Patent: Jul. 17, 2012

(54) INTRAVITREAL INJECTION DEVICE AND SYSTEM

(75) Inventors: Michel Cormier, Mountain View, CA (US); Gholam Peyman, Sun City, AZ (US); Kamran Hosseini, Los Altos, CA (US)

(73) Assignee: KMG Pharma, Inc, Mountain View, CA (US)

( * ) Notice: Subject to any disclaimer, the term of this patent is extended or adjusted under 35 U.S.C. 154(b) by 619 days.

(21) Appl. No.: 12/456,439

(22) Filed: Jun. 16, 2009

(65) Prior Publication Data

US 2010/0100054 A1 Apr. 22, 2010

Related U.S. Application Data

(63) Continuation-in-part of application No. 12/288,510, filed on Oct. 21, 2008, now Pat. No. 7,678,078.

(51) Int. Cl.
*A61M 5/00* (2006.01)
(52) U.S. Cl. ........................ 604/117; 604/116
(58) Field of Classification Search .................. 604/521, 604/68, 116, 117, 289, 294
See application file for complete search history.

(56) References Cited

U.S. PATENT DOCUMENTS

| 4,688,570 | A | * | 8/1987 | Kramer et al. | 606/166 |
| 4,710,176 | A | * | 12/1987 | Quick | 604/177 |
| 4,883,068 | A | * | 11/1989 | Dechow | 600/573 |
| 6,258,067 | B1 | * | 7/2001 | Hill | 604/187 |
| 6,299,603 | B1 | * | 10/2001 | Hecker et al. | 604/181 |
| 6,582,445 | B1 | | 6/2003 | Koons | |
| 7,402,156 | B2 | * | 7/2008 | Kiehlbauch et al. | 604/294 |
| 7,678,078 | B1 | * | 3/2010 | Peyman et al. | 604/117 |
| 2003/0060763 | A1 | * | 3/2003 | Penfold et al. | 604/116 |
| 2006/0047250 | A1 | | 3/2006 | Hickingbotham et al. | |
| 2007/0005016 | A1 | * | 1/2007 | Williams | 604/116 |

FOREIGN PATENT DOCUMENTS

WO WO 2008/084064 7/2008

* cited by examiner

*Primary Examiner* — Kevin Sirmons
*Assistant Examiner* — Andrew Gilbert
(74) *Attorney, Agent, or Firm* — Francis Law Group

(57) ABSTRACT

An intravitreal injection system for administering a pharmacological agent formulation to an intravitreal compartment of an eye, comprising (i) an injection member coupled to, or comprising, an internal formulation chamber that is adapted to receive and contain the pharmacological agent formulation therein, (ii) a needle having a first end that is in communication with a formulation chamber and a second injection end, and (iii) a movable platform for positioning the system on the eye, guiding the needle, and limiting the penetration depth of the needle into the eye.

3 Claims, 13 Drawing Sheets

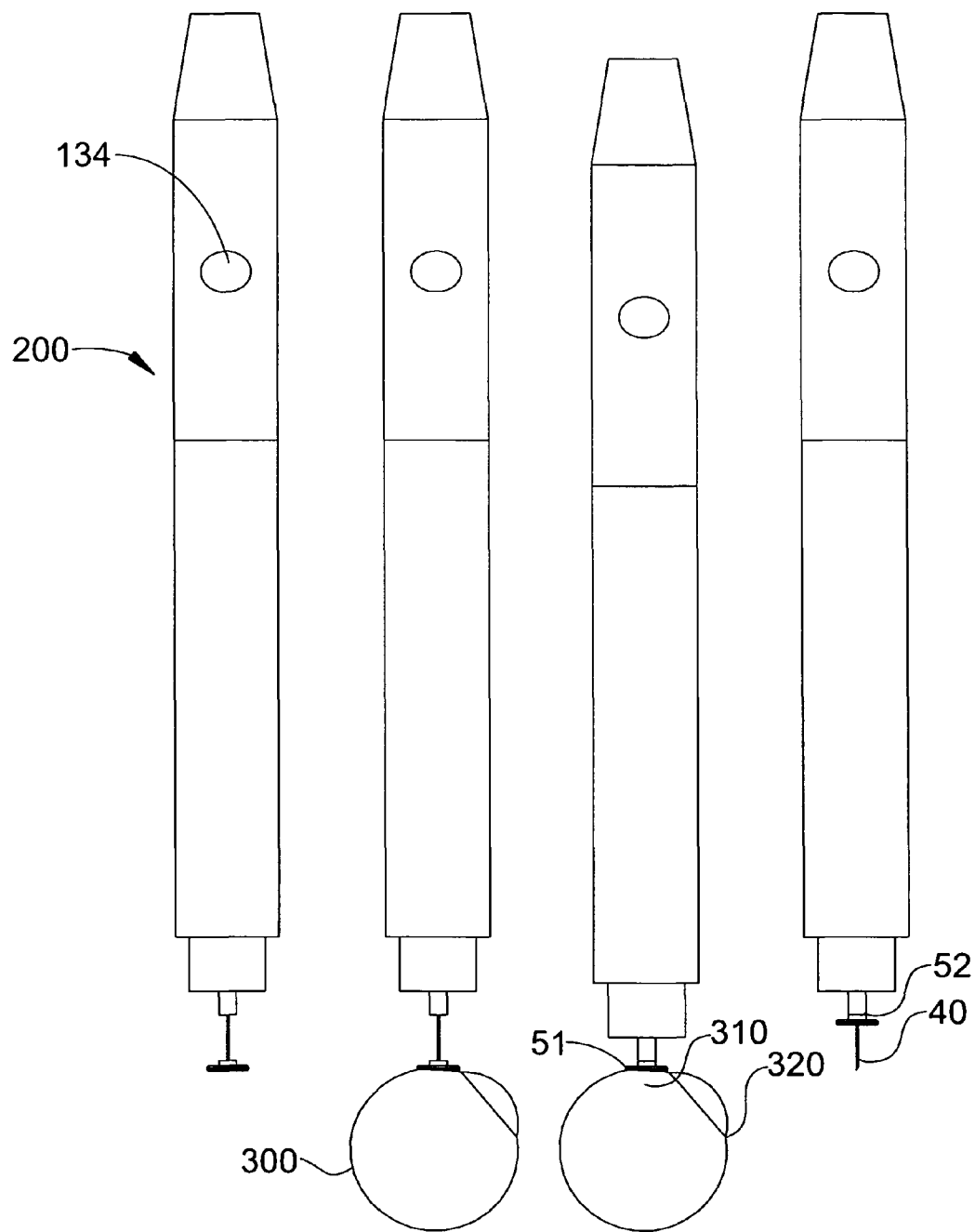
*FIG. 5A*   *FIG. 5B*   *FIG. 5C*   *FIG. 5D*

INTRAVITREAL INJECTION DEVICE AND SYSTEM

CROSS-REFERENCE TO RELATED APPLICATIONS

This application is a continuation-in-part of U.S. application Ser. No. 12/288,510, filed Oct. 21, 2008, now U.S. Pat. No. 7,678,078.

FIELD OF THE INVENTION

This invention relates generally to intravitreal injection as a means of treating various conditions of the eye. More particularly, the invention relates to improved means for performing an intravitreal injection with the benefits of improved safety for the patient and increased efficiency for the practitioner.

BACKGROUND OF THE INVENTION

As is well known in the art, delivery of pharmacological agents (or drugs) to a specific organ or tissue can be achieved through systemic or local administration. In systemic administration, the agent is introduced into the systemic, or general, circulation by ingestion, injection, inhalation or transdermal administration. Circulating blood delivers the agent to the target tissue by either passive or active transport.

Advantages of systemic administration are that this mode of administration, especially by ingestion, is simple and well accepted by the patient. A disadvantage, however, is that the agent must be administered at relatively high doses in order to reach the target area in sufficient quantity. Moreover, the agent is delivered to the entire body, which can include sites where the agent can cause significant side effects. This is especially true for chemotherapeutic agents that tend to present significant systemic toxicity, and steroids, which present significant long-term systemic side effects.

Another significant disadvantage of systemic administration is that transfer of many pharmacological agents from the blood to certain tissues, such as the brain or an eye, is very inefficient.

An alternative to systemic administration is to administer the pharmacological agent(s) into a target organ (or tissue) or in close proximity thereto. However, as is well known in the art, local administration of an agent into or proximate an organ; particularly, an eye, typically requires strict adherence to numerous safeguards.

As discussed in detail herein, the eye is a delicate sense organ that is surrounded by specialized structures and protected by the orbit bones, soft tissues and eyelids. The eye itself is composed of three primary layers: the sclera, the uvea, and the retina. The iris, ciliary body and choroid constitute the uvea.

Blood is transmitted through the choroid and the central retinal artery to the retina. The intraocular pressure (IOP) therein is normally below approximately 20 mm Hg. As is well known in the art, significant elevation of the IOP can, and in many instances will, collapse the choroidal and, subsequently, the retinal circulation. A long standing pressure rise can also cause rapid blindness.

Because of the complex nature of the eye, it is susceptible to a large number of abnormalities (and/or diseases). The abnormalities include dry eye, allergies, infections, various inflammatory diseases and glaucoma.

Treatments of the abnormalities and diseases have, in general, been limited to topical administration of agents or preparations. A conventional example of topical administration of an agent to the eye is the delivery of timolol via eye drops.

As is well known in the art, eye drops facilitate transmission of the agent directly to the anterior part of the eye by instillation into the cul-de-sac. The agents are then moved via the tears of the eye across the cornea and sclera into the anterior and posterior chambers of the eye without initially entering the systemic circulation path.

The advantage of this mode of administration (or delivery) is that the agent is concentrated in the target tissue with a much lower systemic exposure. This tends to reduce the above-mentioned systemic effects.

A disadvantage of this mode of administration is that not all eye tissues are accessible by this route of delivery. Tears can also redirect a significant portion of the agent away from the target area relatively quickly.

A further disadvantage of this mode of administration is that it is mostly applicable to small molecular weight pharmacological agents. Indeed, large molecular weight agents, such as antibodies, are known to diffuse poorly across the cornea or the sclera.

More recently, intravitreal injection methods and systems have been employed to administer agents to the eye to abate abnormalities, such as macular degeneration, diabetic retinopathy and posterior uveitis. The noted agents include steroids, for which long-term systemic side effects are significant, as well as antibodies, which are known to diffuse poorly from the blood into the eye tissues.

Illustrative are the intravitreal injection methods and systems disclosed in U.S. Pat. Pub. Nos. 2003/0060763 A1 and 20070005016 A1. In U.S. Pat. Pub. No. 2003/0060763 an intravitreal injection method and system is disclosed having a plaque containing guide means for location of a needle entry point into the eye, which thereby facilitates such injection. According to the disclosure, the plaque conforms generally to the shape of the cornea and is maintained in place on the eyeball through contact with the eyelids. Injection occurs though a guide within the plate via a conventional needle and syringe.

In U.S. Pat. Pub. No. 2007/0005016 another intravitreal injection method and system is disclosed that is adapted to perform injection within a pars plana portion of the eye using a conventional needle and syringe. The noted application does not, however, disclose any means of safely securing the system to the eye during injection of the agent formulation.

Although the noted intravitreal injection methods and systems represent an improvement over conventional injection with a needle and syringe, there are several disadvantages and shortcomings associated therewith. A major drawback is that the methods and systems disclosed in the noted references, as well as known prior art intravitreal injection methods and systems, do not provide means to properly secure the plate or the frame on the eye.

Further, the noted intravitreal injection methods and systems are not integrated systems and require a number of steps following the placement of the system on the surface of the eye.

Even more recently, intraocular injection using needleless jet injection has been employed to administer agents to the eye. Illustrative are the methods and systems disclosed in U.S. Pat. Pub. Nos. 2007/0052139, 2007/0055199, 2007/0055200, 2007/0055214. There are, however, similarly several disadvantages and drawbacks associate with the disclosed methods and systems. A major disadvantage is that they carry a risk of trauma produced by jet formation inside the eye.

In Co-Pending U.S. application Ser. No. 12/288,510, which is incorporated by reference herein in its entirety, a needle-assisted jet injector is used to minimize the risk of trauma produced by jet formation inside the eye. In the noted application, the range of pressure is reduced, as compared to the pressures used in needleless jet injection. This is accomplished through use of a very short needle that has a limited penetration depth into the eye of about 1 mm. Although the risk of jet formation inside the eye is very low with this device, the risk is not completely eliminated.

Associated with the development of new pharmacological treatments for retinal diseases, vitreoretinal specialists are being faced with the responsibility for providing an ever increasing number of intravitreal injections of pharmacological agents and, hence, addressing the aforementioned issues associated with the prior art intravitreal injection methods and systems.

Further, intravitreal injections cannot always be scheduled in advance and each injection requires several steps to prepare the eye and safely perform the injection. The time required to perform injections can thus disrupt office schedules, resulting in unexpected prolongation of patient waiting times.

Therefore, it would be desirable to provide a method and system to standardize and simplify the intravitreal injection process, improve patient comfort and safety, and increase efficiency of the process.

It is therefore an object of the present invention to provide an intravitreal injection method and system that provides safe, accurate, consistent, and rapid injection of therapeutic agents into the intravitreal compartment of the eye.

It is another object of the present invention to provide an intravitreal injection method and system that facilitates injection of therapeutic agents into the intravitreal compartment of the eye with minimal risk of trauma to a patient's eye.

It is another object of the present invention to provide an intravitreal injection method and system that provides semi-automated injection of therapeutic agents into the intravitreal compartment of the eye.

SUMMARY OF THE INVENTION

In accordance with the above objects and those that will be mentioned and will become apparent below, in one embodiment of the invention, there is disclosed an intravitreal injection system for administering a pharmacological agent formulation to an intravitreal compartment of an eye, comprising (i) an injection member coupled to an internal formulation chamber that is adapted to receive and contain the pharmacological agent formulation therein, (ii) a needle having a first end that is in communication with a formulation chamber and a second injection end, and (iii) a movable guide platform for positioning the system on the eye, guiding the needle, and limiting the penetration depth of the needle into the eye.

In a preferred embodiment of the invention, the intravitreal injection system is adapted to cooperate with an injector, the injector being adapted to expel the pharmacological agent formulation, through manual or automated mechanical force, from the formulation member and through the needle.

In one embodiment of the invention, the system provides a predetermined needle penetration depth into said eye in the range of approximately 1-10 mm.

In one embodiment of the invention, the system includes a fixed platform that cooperates with the moveable guide platform and limits movement of the moveable guide platform.

In one embodiment of the invention, the moveable guide platform includes suction means that provides an engagement force when the guide platform is positioned on the eye.

In another embodiment of the invention, there is disclosed an intravitreal injection system for administering a pharmacological agent formulation to an intravitreal compartment of an eye, comprising (i) an injection member coupled to an internal formulation chamber that is adapted to receive and contain the pharmacological agent formulation therein, (ii) a needle having a first end that is in communication with a formulation chamber and a second injection end, and (iii) a compressible guide platform for positioning the system on the eye, guiding the needle, and limiting the penetration depth of the needle into the eye.

In one embodiment of the invention, the system provides a predetermined needle penetration depth into said eye in the range of approximately 1-10 mm.

In one embodiment of the invention, the compressible guide platform has a substantially circular shape and includes a centrally located lumen that is adapted to receive and guide said needle.

In one embodiment of the invention, the compressible guide platform comprises a non-reticulated closed-cell foam.

In one embodiment of the invention, the compressible guide platform comprises a reticulated open-cell foam.

In one embodiment of the invention, the foam comprises a polymeric material selected from the group consisting of polyvinylchloride, polyurethane, polystyrene, polypropylene, polyethylene, crosslinked polyethylene, ethyl vinyl acetate, polyesters, vinyl nitrile neoprene and mixtures thereof.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 5A is a front plane view of the intravitreal injection device shown in FIG. 4G, according to the invention;

FIG. 5B is a front plane view of the intravitreal injection device shown in FIG. 5A positioned on the pars plana of the eye, according to the invention;

FIG. 5C is a front plane view of the intravitreal injection device shown in FIG. 5A positioned on the pars plana of the eye and having penetrated through the sclera, according to the invention;

FIG. 5D is a front plane view of the intravitreal injection device shown in FIG. 5A after removal from the eye, according to the invention;

DETAILED DESCRIPTION OF THE PREFERRED EMBODIMENTS

Figures 1A, 1B:
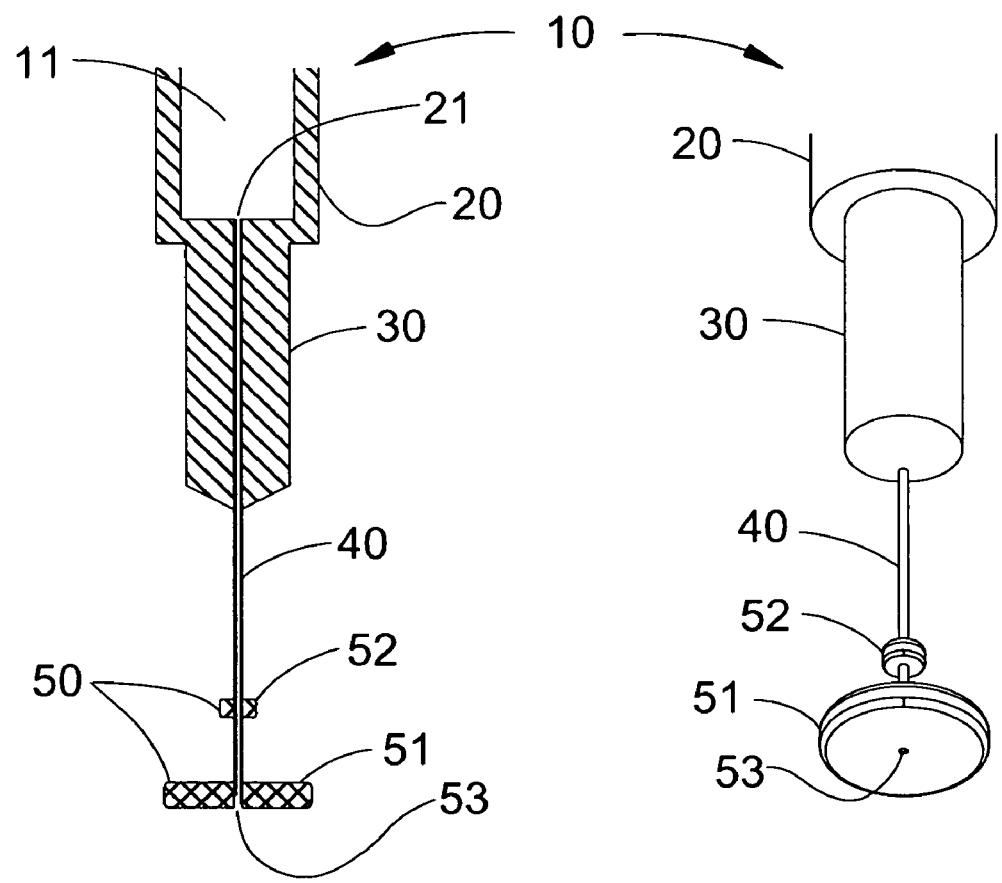
FIG. 1A is a partial cross-sectional, front plane view of an intravitreal injection member, according to one embodiment of the invention.
FIG. 1B is a partial perspective view of the intravitreal injection member shown in FIG. 1A, according to the invention.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise. Thus, for example, reference to "pharmacological agents" includes two or more such agents and the like.

Definitions

The terms "pharmacological agents", "pharmaceutical agent", "agent", "active agent", "drug", and "pharmaceutical composition" are used interchangeably herein and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like. The active drug that can be delivered includes inorganic and organic compounds.

According to the invention, suitable agents can be selected from, for example, small molecules, such as steroids and NSAIDs, proteins, enzymes, hormones, oligonucleotides, polynucleotides, nucleoproteins, modified DNA and RNA loaded viruses with modified capsid, polysaccharides, glycoproteins, lipoproteins, polypeptides, including drug carriers, such as pokymers, micro and nano particles.

Further examples of suitable agents include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, Anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), NT-3, NT-4, NGF, IGF-2, antibiotics or antifungal drugs, anti pain medication, anesthetics, and combinations thereof.

It is to be understood that more than one agent can be combined or mixed together and incorporated into or used by the present invention, and that the use of the terms "pharmacological agent", "pharmaceutical agent", "agent", "active agent", "drug" and "pharmaceutical composition" in no way excludes the use of two or more such "pharmacological agents", "pharmaceutical agents", "agents", "active agents", "drugs", and "pharmaceutical compositions."

The terms "active agent formulation", "drug formulation" and "formulation", as used herein, mean and includes an active agent optionally in combination with one or more pharmaceutically acceptable carriers and/or additional inert ingredients. Example of acceptable carrier include, without limitation, poly(lactic-co-glycolic acid) (PLGA) based microparticles. According to the invention, the formulation can be either in solution or in suspension in the carrier.

The term "movable platform", as used herein, refers to a platform that is totally or partially free to slide along the shaft of a needle.

As used in this application, the term "distal" shall designate the end or direction of injection. The term proximal shall designate the end or direction toward the rear of the injector or toward the rear of the injection member and/or injector and/or injection member.

The present invention substantially reduces or eliminates the disadvantages and drawbacks associated with prior art intravitreal injection methods and systems As discussed in detail herein, the invention is directed to novel agent delivery systems, their methods of manufacture and their methods of use. The invention also provides improved means of performing intravitreal injections with the benefits of improved safety for the patient and increased efficiency for the practitioner.

The following is a brief description of the various anatomical features of the eye, which will help in the understanding of the various features of the invention:

The tear film, which baths the surface of the eye, is about 0.007 mm thick. The volume of the tear film is generally approximately 0.007 mL.

The tear film has many functions, including hydration, providing nutrients to the epithelial layers, lubrication of the eyelid, and cleaning of the surface of the eye. In addition, tear film has antibacterial properties.

The cornea, which is the transparent window that covers the front of the eye, is a lens-like structure that provides two-thirds of the focusing power of the eye. The cornea is covered by an epithelium.

The cornea is slightly oval, having an average diameter of about 12 mm horizontally and 11 mm vertically. The central thickness of the cornea is approximately 0.5 mm and approximately 1 mm thick at the periphery.

The aqueous humor occupies the anterior chamber of the eye. The humor has a volume of about 0.6 mL.

The aqueous humor provides nutrients to the cornea and lens. The humor also maintains normal IOP.

The limbus is the 1-2 mm transition zone between the cornea and the sclera. This region contains the outflow apparatus of the aqueous humor.

The conjunctiva is a thin clear vascular mucous membrane that starts at the limbus and covers the sclera and the inner surface of the eyelid. The conjunctiva is composed of non-keratinized stratified columnar epithelium, which is approximately 3-7 layers thick. The average thickness of the conjunctiva is about 0.05 mm.

The conjunctiva also contains goblet cells that secrete the mucin layer of the tear film, as well as the accessory lachrymal glands of Krause and Wolfring.

The sclera is the white region of the eye, i.e. posterior five sixths of the globe. It is the tough, avascular, outer fibrous layer of the eye that forms a protective envelope. The sclera is mostly composed of dense collagen fibrils that are irregular in size and arrangement (as opposed to the cornea). The extraocular muscles insert into the sclera behind the limbus.

The sclera can be subdivided into 3 layers: the episclera, sclera proper and lamina fusca. The episclera is the most external layer. It is a loose connective tissue adjacent to the periorbital fat and is well vascularized.

The sclera proper, also called tenon's capsule, is the layer that gives the eye its toughness. The sclera proper is avascular and composed of dense type I and III collagen.

The lamina fusca is the inner aspect of the sclera. It is located adjacent to the choroid and contains thin collagen fibers and pigment cells.

The pars plana is a discrete area of the sclera. This area is a virtually concentric ring that is located between 2 mm and 4 mm away from the cornea. This area is devoid of the inner retinal layer, which, as discussed in detail below, makes it a prime target for intraocular injection.

The mean scleral thickness±SD of the pars plana is reported to be approximately 0.53±0.14 mm at the corneoscleral limbus, significantly decreasing to 0.39±0.17 mm near the equator, and increasing to 0.9 to 1.0 mm near the optic nerve. At the location of the pars plana, the thickness of the sclera is about 0.47±0.13 mm.

The thickness of the sclera is known to vary according to sex, age, and is altered in various pathological conditions. Overall, the range of thickness of the sclera at the location of the pars plana is estimated to be in the range of approximately 0.3-1.0 mm. The total thickness of the membranes enclosing the eye cavity, at the location of the pars plana, is estimated to be in the range of approximately 0.5-1 mm.

The uvea refers to the pigmented layer of the eye and is made up of three distinct structures: the iris, ciliary body, and choroid. The iris is the annular skirt of tissue in the anterior chamber that functions as an aperture. The iris root attaches to the ciliary body peripherally. The pupil is the central opening in the iris.

The ciliary body is the 6 mm portion of uvea between the iris and choroid. The ciliary body is attached to the sclera at the scleral spur. It is composed of two zones: the anterior 2 mm pars plicata, which contains the ciliary muscle, vessels, and processes, and the posterior 4 mm pars plana.

The ciliary muscle controls accommodation (focusing) of the lens, while the ciliary processes suspend the lens (from small fibers called zonules) and produce the aqueous humor (the fluid that fills the anterior and posterior chambers and maintains intraocular pressure).

The choroid is the tissue disposed between the sclera and retina. The choroid is attached to the sclera at the optic nerve and scleral spur. This highly vascular tissue supplies nutrients to the retinal pigment epithelium (RPE) and outer retinal layers.

The layers of the choroid (from inner to outer) are: Bruch's membrane, choriocapillaris, and stroma. Bruch's membrane separates the RPE from the choroid and is a permeable layer composed of the basement membrane of each, with collagen and elastic tissues in the middle.

A suprachoroidal space exists between the choroid and sclera. In certain disease processes, fluid or blood can fill this space creating a choroidal detachment.

The crystalline lens, located between the posterior chamber and the vitreous cavity, separates the anterior and posterior segments of the eye. Zonular fibers suspend the lens from the ciliary body and enable the ciliary muscle to focus the lens by changing its shape.

The retina is the delicate transparent light sensing inner layer of the eye. The retina faces the vitreous and consists of 2 basic layers: the neural retina and retinal pigment epithelium. The neural retina is the inner layer. It has 9 layers, including the photoreceptor layer. The retinal pigment epithelium is the outer layer that rests on Bruch's membrane and choroid.

The vitreous is the largest chamber of the eye (i.e. ~4.5 ml). The vitreous is a viscous transparent gel composed mostly of water. It also contains a random network of thin collagen fibers, mucopolysaccharides, and hyaluronic acid.

The vitreous adheres firmly to the margin of the optic disc and to the peripheral retina at the ora serrata and the pars plana. With aging, the vitreous liquefies; a process known as syneresis.

As indicated above, the present invention provides improved means of performing intravitreal injections with the benefits of improved safety for the patient and increased efficiency for the practitioner. The agent delivery system, in accordance with the present invention, is adapted to deliver agents, such as liquid agent formulations, to the intravitreal compartment of a patient by injection of the agent formulation.

According to the invention, the agent formulations can comprise various forms, including, without limitation, solutions and suspensions of various viscosity.

As discussed in detail herein, in one embodiment of the invention, the intravitreal injection system of the invention includes an injection member having a needle and movable platform that is adapted to receive and guide the needle. Preferably, the injection member is sterilized and packaged individually for single use.

In a preferred embodiment of the invention, the assembly of the injector with the injection member is performed prior to application of the assembled intravitreal injection device to the eye.

As discussed in detail below, the movable platform is designed to conform to the surface of the sclera and to provide a support for precise injection at the pars plana site and, in some embodiments, adhesion of the movable platform to the eye.

The invention is also directed to an intravitreal injection assembly or kit, which, in one embodiment of the invention, includes (1) a liquid formulation, i.e. active agent formulation, containing an effective amount of an agent useful for treating a condition of an eye of a patient; (2) an injection member coupled to, or comprising, a formulation member, a needle, and a movable platform, and (3) a injector to facilitate ejection of the pharmacological formulation into and through the injection member. As indicated above, the agent formulation can comprise of various forms, such as solutions and suspensions of various viscosity.

In one embodiment of the invention, the total volume of the active agent formulation to be injected in the intravitreal space is preferably in the range of approximately 0.01-0.2 mL.

Preferably, injection is performed through a very discrete area of the eye, i.e. the pars plana. As indicated above, this area is devoid of the inner retinal layer which makes it a prime target for intraocular injection.

Accordingly, in one embodiment of the invention, the injection member of the invention, i.e. needle, which is described in detail below, has a penetrating length in the range of approximately 1-10 mm. An injection pressure in the range of approximately 5-200 psi is also preferably provided. The noted injection member parameter and injection pressure range has been found to offer the greatest safety for intravitreal administration.

According to the invention, the injector can be powered by manual force, a spring, compressed gas, pyrotechnics, or electricity, such as disclosed in U.S. Pat. Nos. 5,954,689, 5,704,911, 5,505,697, 6,585,685 and 7,150,409; which are incorporated by reference herein.

In an alternative embodiment of the invention, the injector is disposable, as described, for example in U.S. Pat. No. 6,682,504; which is also incorporated by reference herein. As discussed in detail below, in some embodiments, the injection member and injector can be preassembled and ready for use without any further assembly.

In one embodiment of the invention, the injector is capable of producing pressure in the range of approximately 5-200 psi (measured as the force of the fluid stream divided by the cross-sectional area of the fluid stream).

Referring now to FIGS. 1A and 1B, there is shown one embodiment of an injection member of the invention. As illustrated in FIG. 1A, the injection member 10 includes a formulation member 20 having an internal formulation chamber 11 that is adapted to receive a pharmacological formulation therein. The formulation member 20 further includes an opening (or lumen) 21 at the distal end that is in communication with the formulation chamber 11 and is adapted to receive a fixed tubular insert or hollow needle 40.

The injection member also includes a needle holder 30, which is also adapted to receive and to secure the hollow needle 40. Preferably, the needle 40 has an outer diameter in the range of approximately 0.5-0.05 mm and an inner diameter in the range of approximately 0.25-0.025 mm.

The injection member 10 also includes the movable platform means 50 comprising, a slidable platform 51 and a fixed platform 52. According to the invention, the slidable platform 40, is preferably disposed proximate the distal end of the needle 40, as illustrated in FIGS. 1A and 1B. The fixed platform is located along the shaft of the needle 40. In the illustrated embodiment, platforms 51 and 52 have a substantially circular shape and include a centrally located lumen 53 that is adapted to receive the needle 40 and guide the needle into the eye.

As indicated above, in a preferred embodiment of the invention, the needle 40 has a penetrating length in the range of approximately 1-10 mm. The term "penetrating length" length refers to the actual length of the needle 40 that is allowed to penetrate the eye tissue. According to the invention, the actual length of the needle 40 can be longer than the penetrating length.

Preferably, to minimize the risk of eye injury during positioning on the surface of the eye, the needle is not exposed outside the movable platform boundaries. Alternatively, the end of the needle may protrude by up to 2 mm outside the movable platform boundaries.

According to the invention, the needle 40 can comprise a suitable metal, such as stainless steel, or other suitable materials, such as a polymeric material.

Figures 2A, 2B, 2C, 2D, 2E:
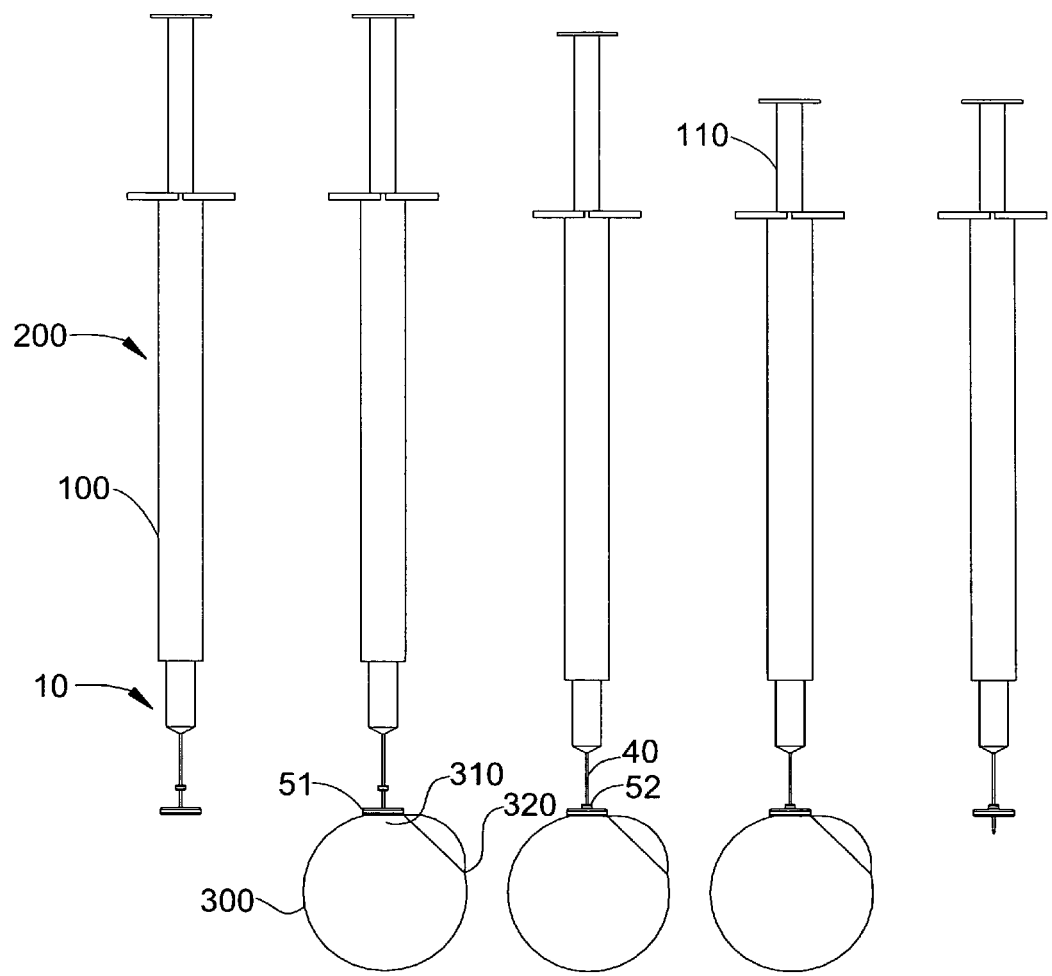
FIG. 2A is a front plane view of the intravitreal injection device the is partially shown in FIG. 1B, according to the invention.
FIG. 2B is a front plane view of the intravitreal injection device shown in FIG. 2A positioned on the pars plana of an eye, according to the invention.
FIG. 2C is a front plane view of the intravitreal injection device shown in FIG. 2A positioned on the pars plana of the eye and penetrating through the sclera, according to the invention.
FIG. 2D is a front plane view of the intravitreal injection device shown in FIG. 2A positioned on the pars plana of the eye, penetrating through the sclera and following injection, according to the invention.
FIG. 2E is a front plane view of the intravitreal injection device shown in FIG. 2A after removal from the eye, according to the invention.

Referring now to FIG. 2A, there is shown the injection member 10 being an integral part of the injector 100, in this case a conventional manually piston-driven syringe, to constitute the device 200. According to the invention, at the time of use, the prefilled sterile device 200 is taken out of its packaging and is positioned on the eye 300. To do so, the slidable platform 51 is positioned on the pars plana area 310 of the eye 300 by positioning of the edge of the slidable platform 51 at the limbus 320. Following positioning of the movable platform on the pars plana area 310, the device 200 is pushed toward the eye which results in the fixed needle 40 penetrating inside the eye tissue, while the slidable platform 51 is allowed to slide alongside the shaft of the needle 40 until it is stopped by the fixed platform 52, as illustrated in FIG. 2C.

Referring to FIG. 2D, there is shown device 200 following injection of the agent formulation into the intravitreal cavity through manual actuation of the piston 110. FIG. 2E illustrates device 200 following injection and removal from the eye and showing the final position of the slidable platform 51 against the fixed platform 52.

The precise positioning of the needle 40, which is achieved by virtue of device 200, substantially reduces the risk of injury to major structures of the eye 300, including the retina, lens, and ciliary body.

Figures 3A, 3B, 3C, 3D:
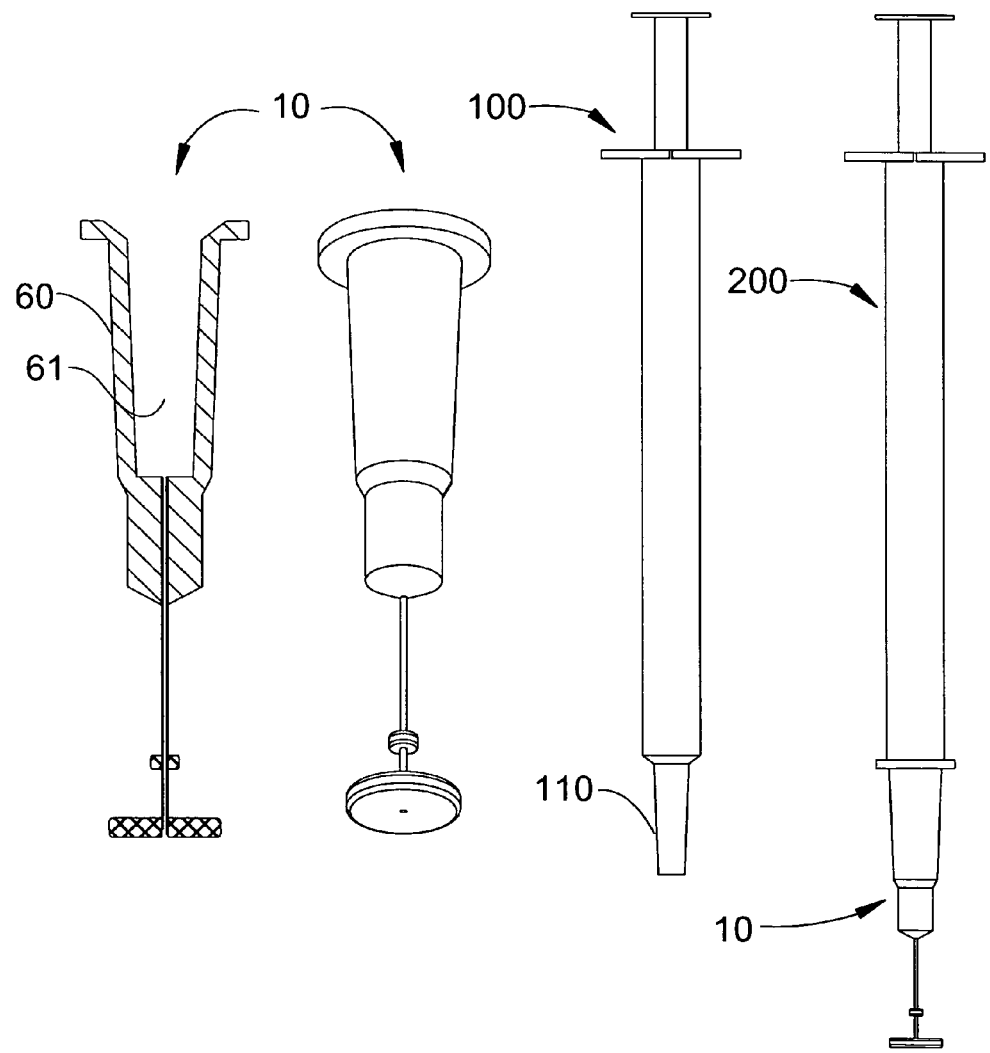
FIG. 3A is a cross-sectional, front plane view of an intravitreal injection member, according to the invention.
FIG. 3B is a perspective view of the intravitreal injection member shown in FIG. 3A, according to the invention.
FIG. 3C is a frontal view of an injection syringe, according to the invention.
FIG. 3D is a frontal view of the injection syringe shown in FIG. 3C assembled with the intravitreal injection member shown in FIG. 3A, according to the invention.

In another embodiment of the invention, shown in FIG. 3A through FIG. 3D, the injection member 10 shown in FIGS. 3A and 3B has a connection member 60 that is adapted to connect to the formulation chamber of an injector through a cavity 61. The injection member 10 is preferably sterilized and packaged individually for single use.

According to the invention, at the time of use, the injector 100, in this case a conventional syringe shown in FIG. 3D, is filled with the appropriate amount of agent formulation and the injection member 10 is thereafter assembled with the injector 100 through conventional means, such as a tight-fitting 110 or a Luer lock (not shown). The final device 200 is shown in FIG. 3D. The injection steps for injection into the intravitreal cavity of the eye are essentially the same as described above and shown in FIGS. 2A through 2E.

Referring now to FIGS. 4A through 4F, there is shown another embodiment of an injection member of the invention for use with a replaceable or disposable cartridge. In the illustrated embodiment, the injection member 10 has a connection member 60 that is adapted to connect to the outer body of an injector through a cavity 61. According to the invention, the agent formulation is preferably contained in the cartridge 70 shown in FIG. 4D.

Figures 4A, 4B:
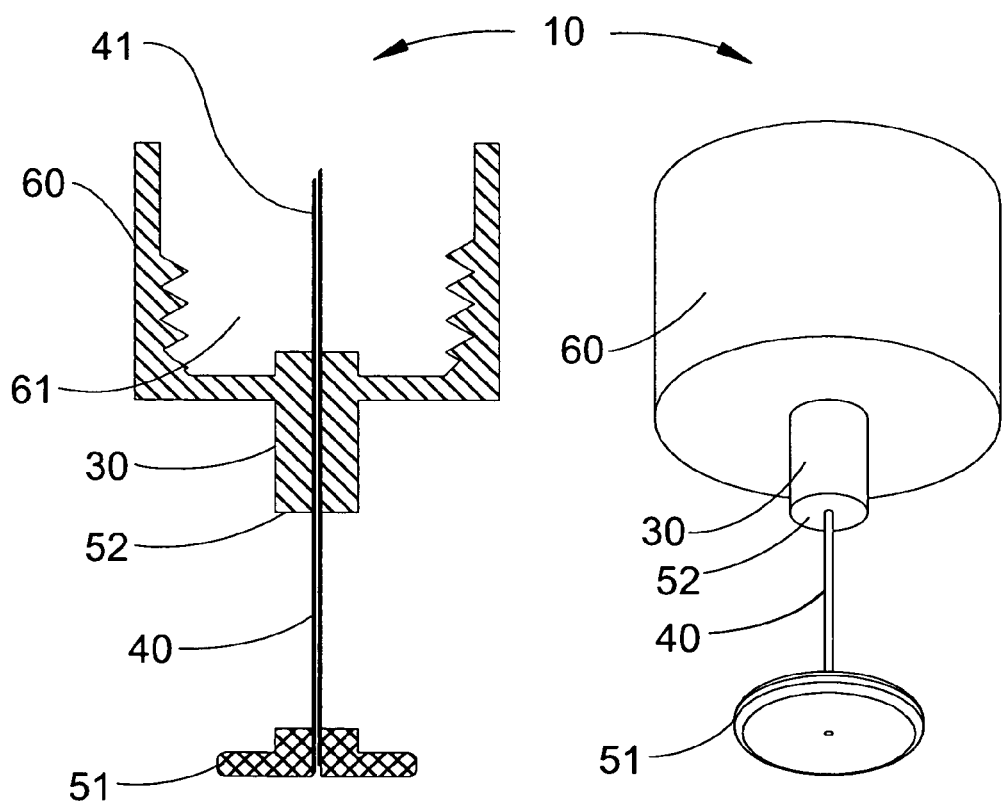
FIG. 4A is a cross-sectional, front plane view of an intravitreal injection member, according to the invention.
FIG. 4B is a perspective view of the intravitreal injection member shown in FIG. 4A, according to the invention.
Figures 4C, 4D, 4E, 4F, 4G:
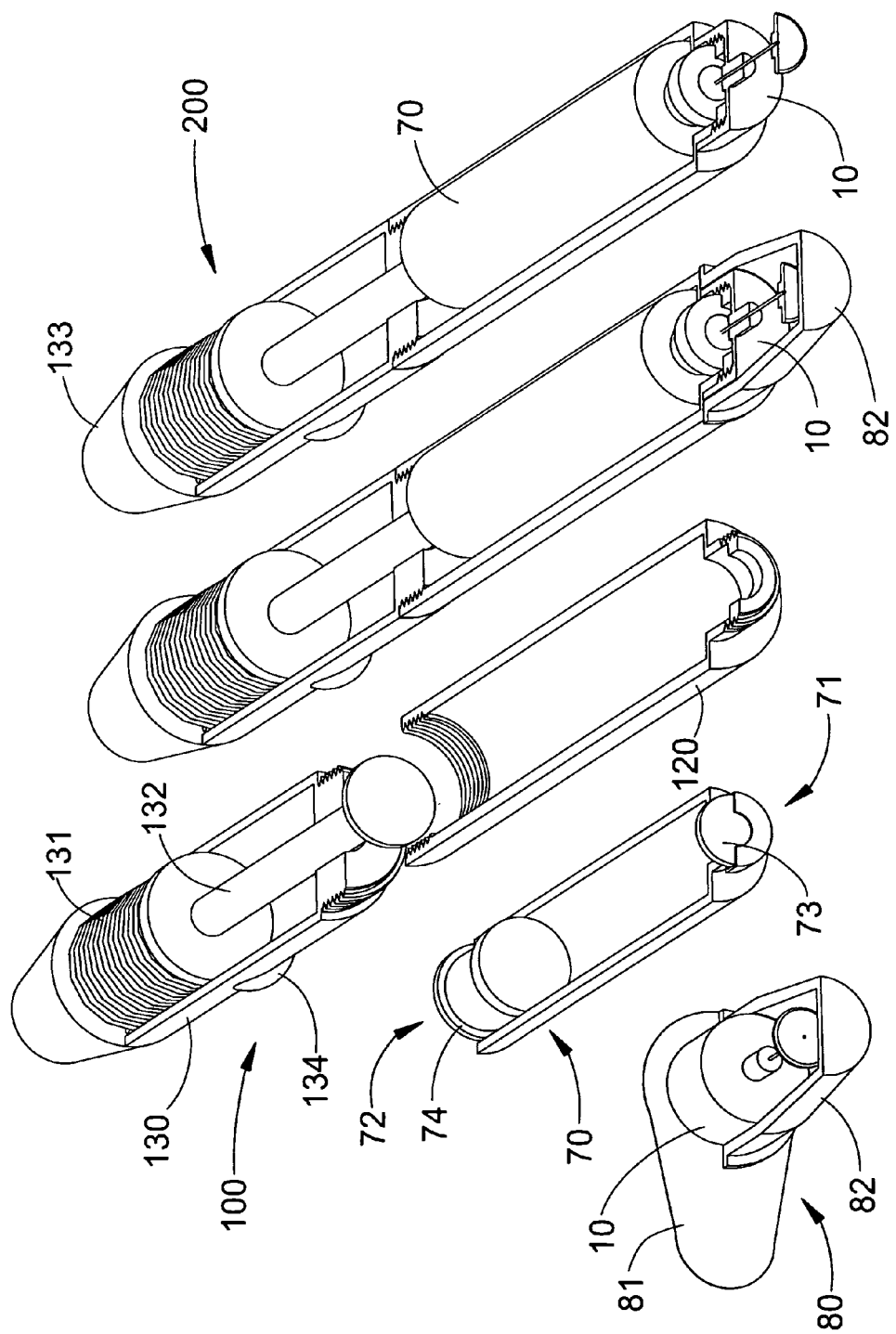
FIG. 4C is a partial cross-sectional, perspective view of the intravitreal injection member shown in FIG. 4A, illustrating one embodiment of packaging therefore, according to the invention.
FIG. 4D is a partial cross-sectional, perspective view of an injection cartridge for use in conjunction with the intravitreal injection member shown in FIG. 4A, according to the invention.
FIG. 4E is a partial cross-sectional, perspective view of a disassembled injector, according to the invention.
FIG. 4F is a partial cross-sectional, perspective view of an assembled injector containing the injection cartridge shown in FIG. 4D and assembled with the intravitreal injection member shown in FIG. 4C, according to the invention.
FIG. 4G is a partial cross-sectional, perspective view of the assembled injector shown in FIG. 4F after removal of the protective packaging, according to the invention.

Referring to FIG. 4D, the cartridge 70 preferably includes a distal end 71, a proximal end 72; each end having an opening therethrough, a pierceable seal 73 that is associated with the opening in the distal end 71; and a stopper 74 that is disposed in the proximal end 72 of the cartridge 70. The stopper 74 is preferably sized and adapted to seal the opening at the proximal end 72 of the cartridge 70 and slide within the cartridge 70.

The replaceable or disposable cartridge is preferably designed and adapted to receive and contain one dose or multiple doses of the agent formulation.

Referring to FIG. 4A, the injection member 10 comprises an injection assisted needle 41 that cooperates with needle 40. As illustrated in FIG. 4A, needle 41 is preferably directed toward the proximal side of the injection member 10.

According to the invention, the injection assisted needle 41 and needle 40 can comprise an integral component. The injection assisted needle 41 can also have the same gauge as the needle 40, as depicted in FIG. 4A, or can have a different gauge.

The injection member 10 also includes a movable platform means, comprising, a slidable platform 51 and a fixed platform 52. In this embodiment, the fixed platform 52 is an integral part of the needle holder 40.

According to the invention, at the time of use, and as depicted in FIGS. 4E and 4F, the cartridge 70 is placed inside the body 120 of the injector 100. The assembly is then secured to the power unit 130 of the injector 100. Referring now to FIG. 4C, there is shown the injection member 10 in a sterile packaging 80.

The releasing tab 81 of the packaging 80 containing the injection member 10 is then pulled out and the injection member still contained in the remainder of the packaging 82 is then pushed manually toward the distal end of the injector and screwed into place, whereby the injection assisting needle 41 pierces the seal 73, as depicted in FIG. 4F. Priming of the injector and adjustment of the dose to be delivered is accomplished by rotating the knob 133. The packaging 82 of the injection member 10 is subsequently removed immediately prior to application to the eye, as illustrated in FIG. 4G, yielding the final device 200.

Activation of the power unit 130, i.e. force generating source, in this case a spring 131, of the injector 100 is accomplished by depressing the actuation button 134, which triggers the spring 131 to move the piston 132 towards the distal end of the injector 100 and, thereby, stopper 74 towards the distal end of the injection member 10, whereby the agent formulation is directed into and through the injection assisting needle 41 and needle 40.

Referring now to FIG. 5A, there is shown the device 200 prior to injection. FIG. 5B depicts the same device with the slidable platform 51 positioned on the pars plana 310 area of the eye 300 following positioning of the edge of the slidable platform 51 at the limbus 320. FIG. 5C illustrates the same device 200 following penetration of the fixed needle 40 of the injection member until penetration is stopped by the fixed platform 52 and following injection of the agent formulation into the intravitreal cavity through actuation of the power unit of the injector, which is accomplished by pressing the actuation button 134. FIG. 5D illustrate device 200 following injection and removal from the eye and showing the final location of the slidable platform 51 positioned along the shaft of the needle 40 and against the fixed platform 52.

In other embodiments of the invention, piercing of the seal 73 is accomplished via the action of inserting the cartridge 70 in the body 120 of the injector 100 following assembly of the injection member 10 to the body 120 of the injector 100 or is accomplished by the force generating source of the injector 100.

According to the invention, the injection member 10 can comprise various polymeric materials, metals and/or metal alloys. In one embodiment of the invention, the formulation member 10 is constructed of a molded polymeric material, such as polyethylene, polystyrene, or polyvinyl chloride.

The slidable platform 51 is preferably composed of thin (i.e. ~0.1-2 mm) elastic biocompatible polymeric material. Preferably, the polymeric material comprises an elastomer, such as natural rubber, synthetic rubber, polybutadiene, nitrile rubber, neoprene, silicone rubber, and ethylene vinyl acetate.

In one embodiment, the movable platforms of the invention are constructed of a transparent polymer, such as transparent thermoplastic polyurethane elastomers. Alternatively, the slidable 51 is composed of tough, closed-cell flexible foam and the distal and/or the proximal parts of the movable platform can be covered with a different polymeric material, such as rubber.

According to the invention, the fixed platform 52 can comprise various polymeric materials, metals and/or metal alloys. In one embodiment of the invention, the fixed platform 52 is constructed of a molded polymeric material, such as polyethylene, polystyrene, or polyvinyl chloride.

According to the invention, the eye-contacting movable platforms 51 (and movable platforms 54, and 59a, discussed in detail below) are designed and configured to conform to the surface of the eye, i.e. preferably include a concave eye contact region, and can comprise various shapes and dimensions as those disclosed in Co-Pending U.S. application Ser. No. 12/288,510, which is incorporated by reference herein in its entirety.

In one embodiment, the movable platform 51 has a substantially circular shape and includes a centrally located lumen 53 that is adapted to receive and guide the needle 30. In one embodiment, the eye-contacting movable platforms of the invention have a diameter in the range of approximately 4-8 mm.

In one embodiment of the invention, the eye-contacting movable platforms of the invention include suction means, such as those disclosed in Co-Pending U.S. application Ser. No. 12/288,510. As set forth in the noted Co-Pending Application, suction means provide an engagement force when the movable platform is positioned on the eye. Examples of suitable suction means include, without limitations, suction cups and suction rings.

In one embodiment of the invention, the needle 40 is preferably disposed orthogonal to the movable platform 51. However, according to the invention, the needle 40 need not be disposed orthogonal to the movable platform 51, but can be at an additional angle of up to 30°. The noted angular positioning reduces the risk of internal ocular injury; particularly, with regards to the lens.

According to the invention, at the time of intraocular injection, placement of the edge of the movable platforms of the invention at the location of the corneoscleral limbus allows precise positioning and application of the needle 40 to the pars plana area.

When resting on the conjunctiva, the movable platforms of the invention, i.e. movable platforms 51, 54, and 59a, act as a guide for the needle 40 and as a soft and non-abrasive support for the injector, thereby eliminating guesswork by the practitioner. The noted movable platforms of the invention also prevent superficial eye injury that could result from contact of the surface of the eye with the distal end of the formulation member of conventional injectors.

In addition, the movable platforms of the invention help assure orthogonality of the injector 100 relative to the surface of the eye and stabilization of the injector 100 at the time of injection.

Figures 6A, 6B:
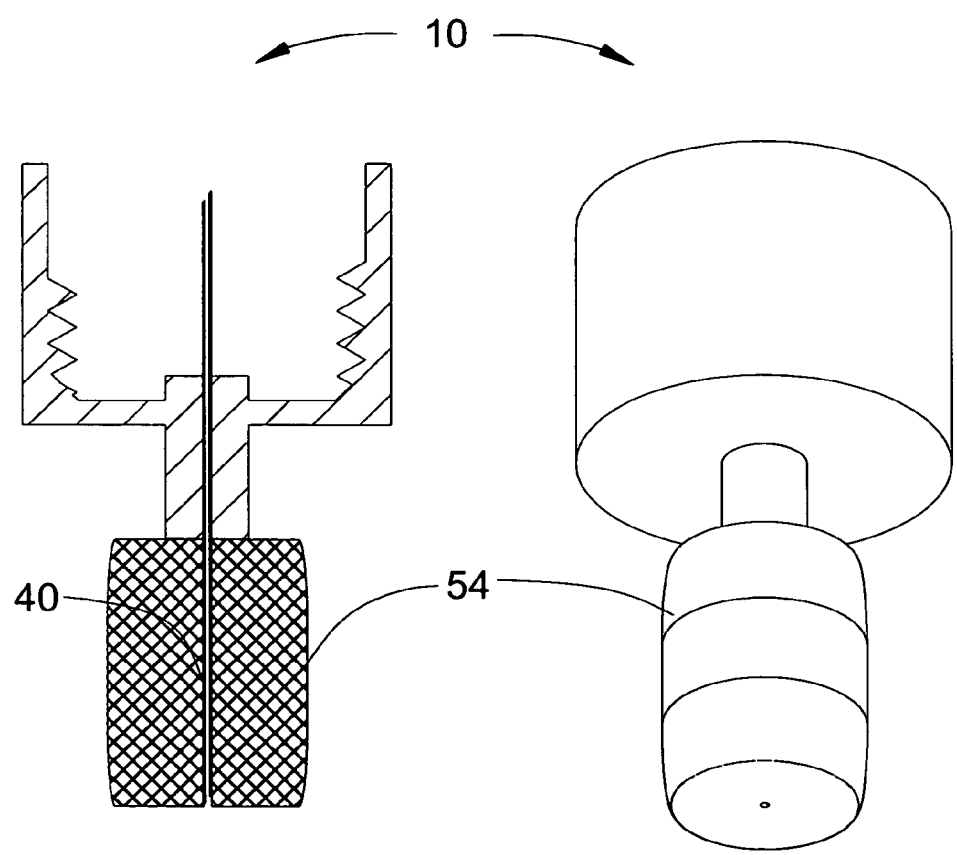
FIG. 6A is a partial cross-sectional, front plane view of an intravitreal injection member, according to another embodiment of the invention.
FIG. 6B is a perspective view of the intravitreal injection member shown in FIG. 6A, according to the invention.

Referring now to FIGS. 6A and 6B, there is shown another embodiment of an injection member 10 of the invention for use with a replaceable or disposable cartridge 70, as described above. A compressible platform 54 is preferably disposed proximate the distal end of the needle 30, as illustrated in FIGS. 6A and 6B.

Figures 7A, 7B, 7C, 7D:
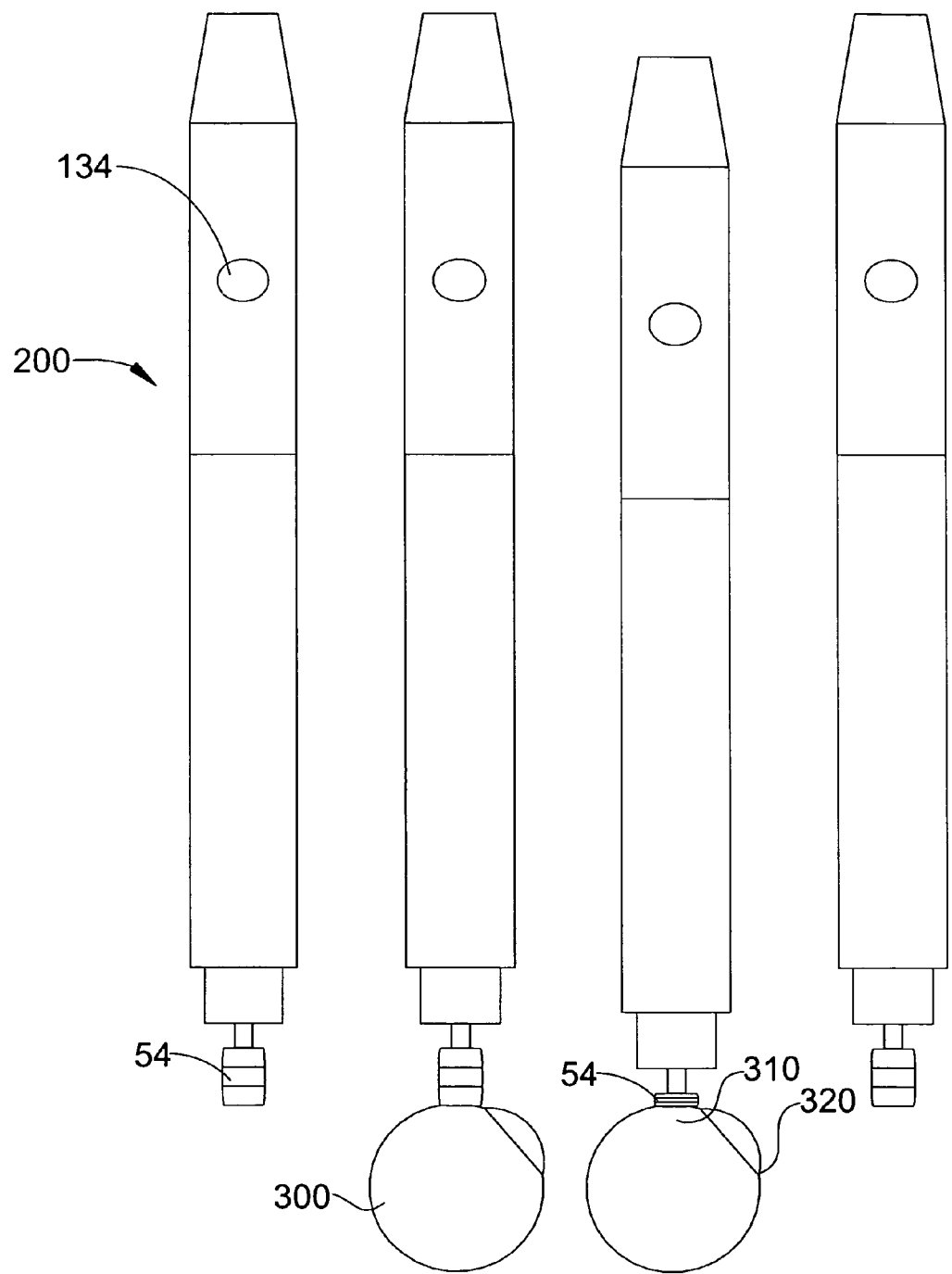
FIG. 7A is a front plane view of an intravitreal injection device, according to another embodiment of the invention.
FIG. 7B is a front plane view of the intravitreal injection device shown in FIG. 7A positioned on the pars plana of the eye, according to the invention.
FIG. 7C is a front plane view of the intravitreal injection device shown in FIG. 7A positioned on the pars plana of the eye and having penetrated through the sclera, according to the invention.
FIG. 7D is a front plane view of the intravitreal injection device shown in FIG. 7A after removal from the eye, according to the invention.

Referring now to FIG. 7A, there is shown the device 200 prior to injection. FIG. 7B depicts the same device with the compressible platform 54 positioned on the pars plana area of the eye 300 following positioning of the edge of the compressible platform 41 at the limbus 440. FIG. 7C illustrates the same device 200 following penetration of the fixed needle 30 of the injection member until penetration is stopped by complete compression of the compressible platform 54 and following injection of the agent formulation into the intravitreal cavity through actuation of the power unit through the actuation button.

FIG. 7D illustrates device 200 following injection and removal from the eye. FIG. 7D also illustrates that, following removal of the device from the eye, the compressible platform 54 is able to transition back to its original shape by virtue of its elastic properties and thereby provides additional safety against needle injury to the patient and the practitioner.

In at least one embodiment, the compressible platform 54 is preferably composed of open-cell foam with a thickness in the range of approximately 2-12 mm. The distal part of the platform can also be covered with a different polymeric material, such as soft rubber. According to the invention, the proximal part of the platform can be composed of hard plastic or tough elastomeric materials. Further, the foam layer need not exhibit the same strength everywhere within the platform.

In some embodiments of the invention, the platform is preferably composed of flexible reticulated cell foam made of polymeric materials, such as polyvinylchloride, polyurethane, polystyrene, polypropylene, polyethylene, crosslinked polyethylene, Ethyl Vinyl Acetate, polyesters, vinyl nitrile neoprene and mixtures thereof. Alternatively other types of foams or cushion materials may be used. The foam may be non-reticulated (closed-cell) or reticulated (open-cell), depending upon the softness of the foam and other parameters.

In some embodiments, the compressible platform possesses elastic properties and is able to return to its original shape once the compression force is removed. In other embodiments, the compressible platform does not possess elastic properties and is able to collapse to a disc and does not return to its original shape once the compression force is removed. An example of a material that can be used to manufacture collapsible platforms is expanded polystyrene.

Figures 8A, 8B, 8C, 8D, 8E:
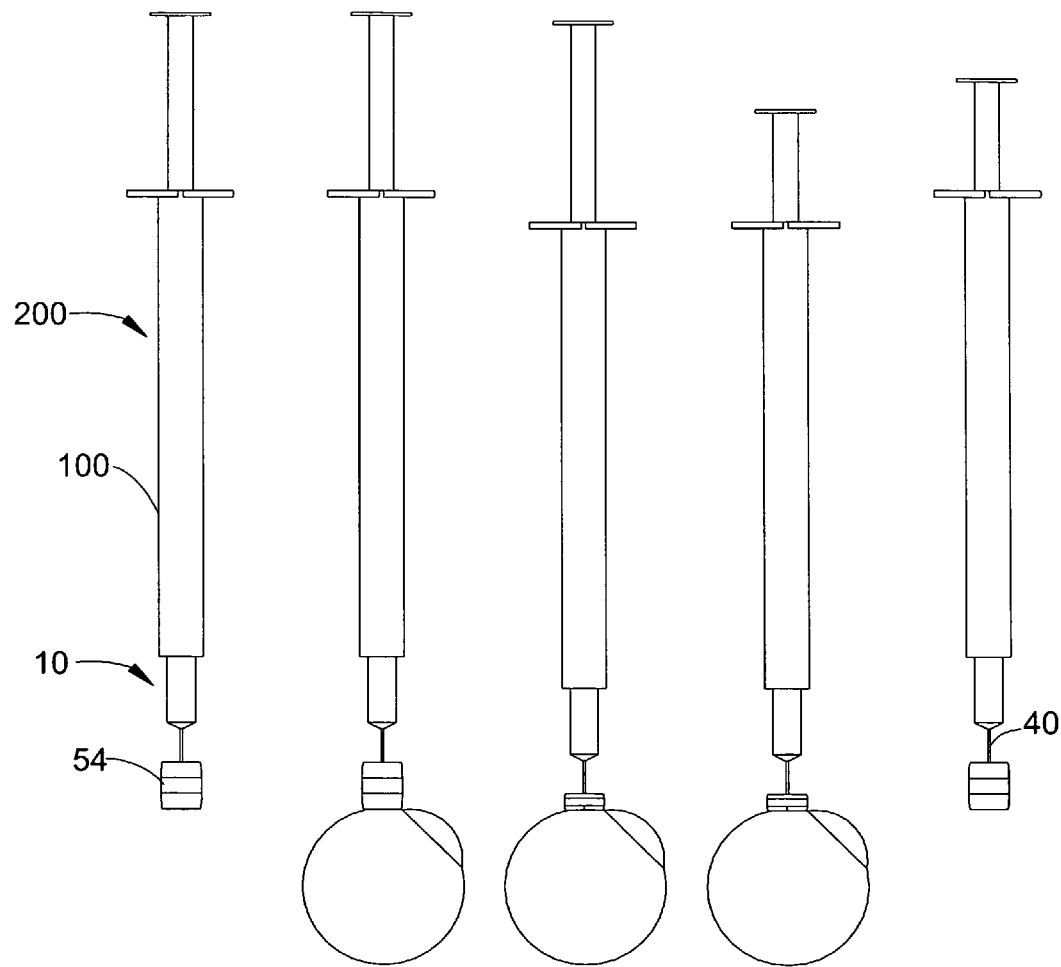
FIG. 8A is a front plane view of an intravitreal injection device, according to another embodiment of the invention.
FIG. 8B is a front plane view of the intravitreal injection device shown in FIG. 8A positioned on the pars plana of the eye, according to the invention.
FIG. 8C is a front plane view of the intravitreal injection device shown in FIG. 8A positioned on the pars plana of the eye and having penetrated through the sclera, according to the invention.
FIG. 8D is a front plane view of the intravitreal injection device shown in FIG. 8A positioned on the pars plana of the eye, penetrating through the sclera and following injection, according to the invention.
FIG. 8E is a front plane view of the intravitreal injection device shown in FIG. 8A after removal from the eye, according to the invention.

In another embodiment of the invention, shown in FIG. 8A, the uppermost part of the compressible platform 54 is securely fixed to the shaft of a needle. The top, distal part of the compressible or collapsible platform is preferably secured to the needle using known bonding agents and operates as a penetration depth limiter. The injection steps for injection into the intravitreal cavity of the eye, illustrated in FIGS. 8A through 8E, are essentially the same as described above and shown in FIGS. 2A through FIG. 2E.

Figures 9A, 9B:
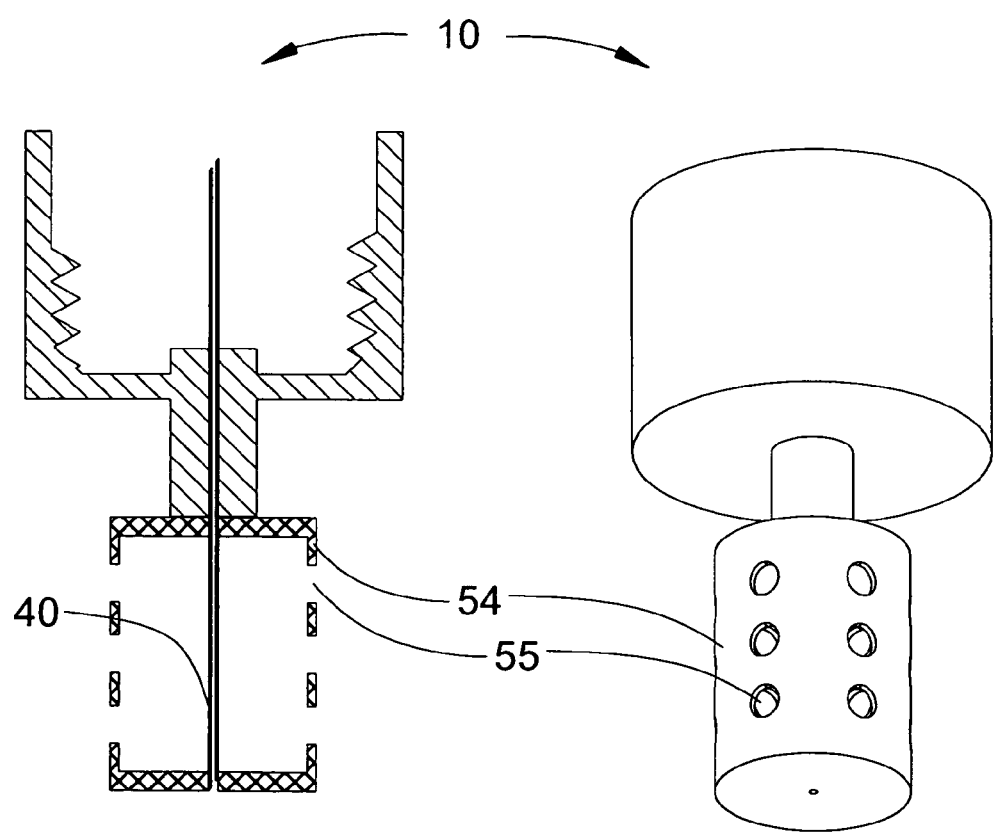
FIG. 9A is a partial cross-sectional, front plane view of an intravitreal injection member, according to another embodiment of the invention.
FIG. 9B is a partial perspective view of the intravitreal injection member shown in FIG. 9A, according to the invention.

In another embodiment of the invention, illustrated in FIGS. 9A and 9B, the compressible platform 54 is hollow and is preferably composed of elastomeric materials. According to the invention, the platform 54 can also include orifices 55. The orifices 55 act as vents for evacuation of the gas contained in the cavity during compression of the platform. The proximal part of the platform can similarly be composed of hard plastic or tough elastomeric materials.

In another embodiment of the invention, illustrated in FIGS. 10A through 10F, the elastic properties of the compressible platform 54 are improved by inclusion of a spring 56 within the platform.

Figure 10A:
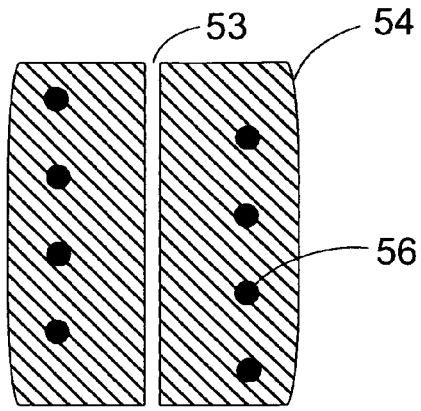
FIG. 10A is a cross-sectional, front plane view of one embodiment of an intravitreal injection compressible platform, according to the invention.
Figure 10B:
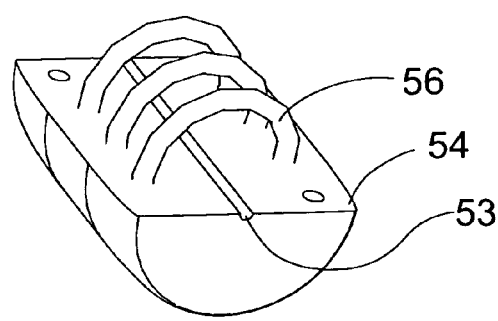
FIG. 10B is a partial cross-sectional, perspective view of the intravitreal injection compressible platform shown in FIG. 10A, according to the invention.

As illustrated in FIGS. 10A and 10B, the spring 56 can be embedded in a compressible solid platform similar to the platform shown in FIGS. 6A and 6B.

Figure 10C:
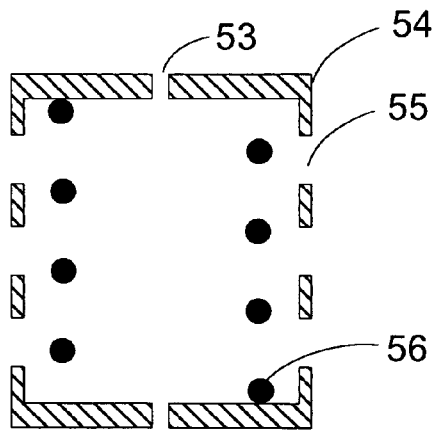
FIG. 10C is a cross-sectional, front plane view of another embodiment of an intravitreal injection compressible platform, according to the invention.
Figure 10D:
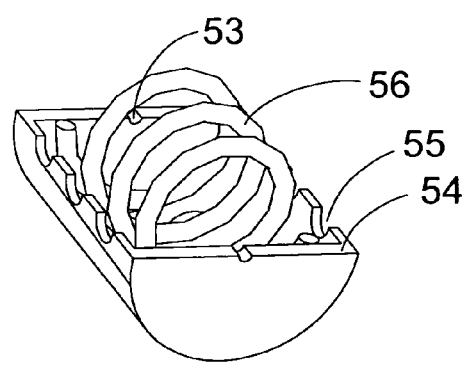
FIG. 10D is a partial cross-sectional, perspective view of the intravitreal injection compressible platform shown in FIG. 10C, according to the invention.

Alternatively, as illustrated in FIGS. 10C and 10D, the spring 56 can be contained in a compressible hollow platform similar to the platform shown in FIGS. 9A and 9B.

Figure 10E:
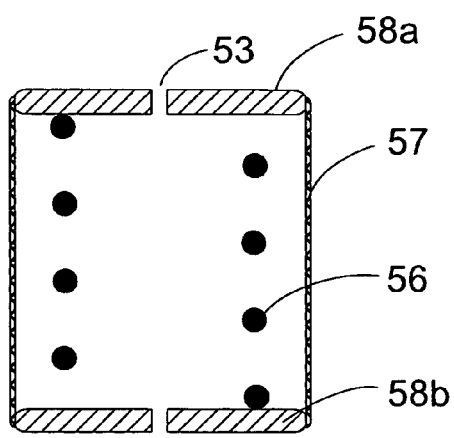
FIG. 10E is a cross-sectional, front plane view of another embodiment of an intravitreal injection compressible platform, according to the invention.
Figure 10F:
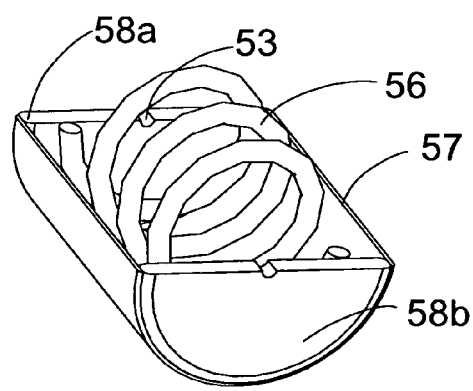
FIG. 10F is a partial cross-sectional, perspective view of the intravitreal injection compressible platform shown in FIG. 10E, according to the invention.

In an alternative embodiment, the spring is caged in a deformable inert material 57 and sandwiched between two uncompressible platforms 58a and 58b, as illustrated in FIGS. 10E and 10F.

Figure 11A:
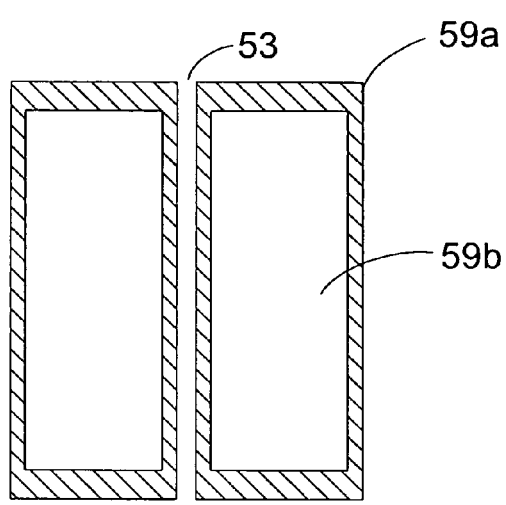
FIG. 11A is a cross-sectional, front plane view of another embodiment of an intravitreal injection compressible platform, according to the invention.
Figure 11B:
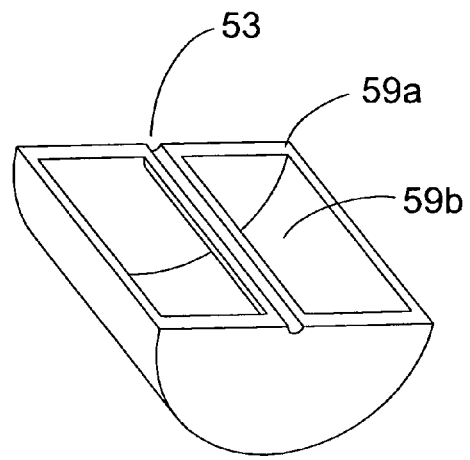
FIG. 11B is a cross-sectional perspective view of the intravitreal injection compressible platform shown in FIG. 11A, according to the invention.

In another embodiment, illustrated in FIGS. 11A and 11B, an enclosed airtight air chamber 59b is located within an elastic compressible platform 59a. The gas contained in the air chamber 59b acts like a spring when the platform is compressed.

As compared to the slidable platform, one of the advantages of the compressible platform is that following injection and removal of the device from the eye, the platform may be able to go back to its initial shape, thereby providing decrease in the risk of needle injury to the patient and the practitioner.

Figure 12:
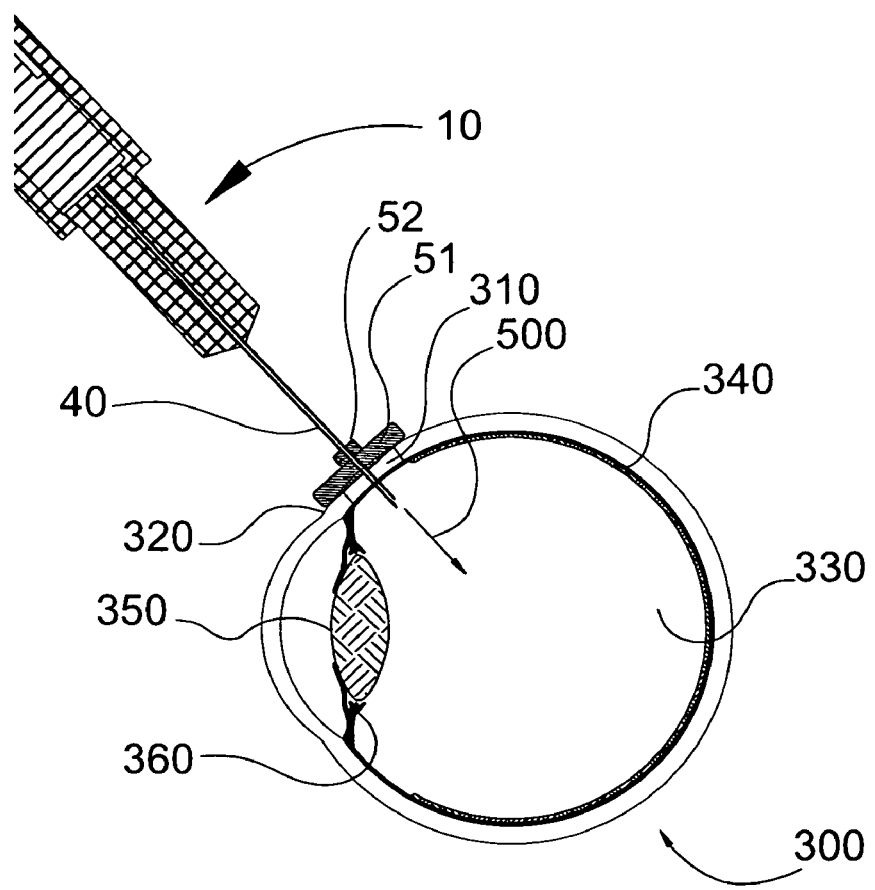
FIG. 12 is a side plane view of one embodiment of an intravitreal injection member applied to the eye, according to the invention.

Referring now to FIG. 12, there is shown a cross section of the eye 300 having an injection member 10 of the invention positioned thereon, i.e. after insertion of the needle 40 in the pars plana area 310 following positioning of the edge of the slidable platform 51 at the limbus 320 and sliding of the slidable platform 51 against the fixed platform 52. FIG. 10 also illustrates the direction of the agent formulation 500 into the vitreous cavity 330. As discussed in detail above, precise positioning of the needle 40 and the shallow penetration thereof substantially reduces the risk of injury to major structures of the eye 300, including the retina 340, lens 350, and ciliary body 360.

As indicated above, the injector 200 can be a disposable unit, and the injection member 10 can be preassembled thereon and ready for use without any further assembly.

In some embodiments of the invention, the injection member 10 also includes a removable safety cap at its distal end. In some embodiments of the invention, the injection member 10 further includes a removable cap at its proximal end.

EXAMPLES

The following examples are given to enable those skilled in the art to more clearly understand and practice the present invention. They should not be considered as limiting the scope of the invention but merely as being illustrated as representative thereof.

Example 1

A cylinder having a diameter of 6 mm and a thickness of 1.75 mm was cut out from a synthetic rubber band. A smaller 3 mm cylinder was cut out of the same material. The smaller cylinder (fixed platform) was pierced in its center with a 29 gauge needle and moved 7 mm along the shaft of the needle and away from the needle tip. It was secured to the shaft of the needle using cyanoacrylate glue. The larger cylinder (movable platform) was subsequently pieced in its center by the same 29 gauge needle until the tip of the needle was apparent on the other side of the cylinder. The assembly was as depicted in FIG. 3A and FIG. 3B and was stored until use.

For testing, a 1 mL syringe was filled with a food grade Deep Blue Shade solution and the assembly of FIG. 3A and FIG. 3B was assembled to the prefilled syringe, as depicted in FIG. 3D. The prefilled device was purged of residual air and positioned on an enucleated albino rabbit eye. To do so, the slidable platform was positioned on the pars plana area of the eye by positioning of the edge of the slidable platform at the limbus. Following positioning of the movable platform on the pars plana area, the device was pushed toward the eye which resulted in the fixed needle penetrating inside the eye tissue while the slidable platform was allowed to slide alongside the shaft of the needle until it was stopped by the fixed platform. Injection of 0.1 mL was subsequently achieved by pushing the piston of the syringe until the desired volume was injected and the device was subsequently pulled out of the eye. These steps are illustrated in FIG. 2B through FIG. 2E. The experiment was repeated in 3 additional enucleated rabbit eyes using identical devices.

Following the experiment, observation of the eyes demonstrated successful intravitreal injections as evidenced by the blue color visible from the corneal side of the eyes. Subsequent dissection confirmed the observation. Minimal contamination of the conjunctiva at the pars plana area was also noted.

This example confirmed the usefulness of the invention using a conventional syringe and needle equipped with a movable platform for precise and easy application to the pars plana area and injection of drug substances into the vitreous.

Example 2

A synthetic rubber cylindrical movable platform having a diameter of 6 mm and a thickness of 1.75 mm was pieced in its center by a 31 gauge pen-needle until the tip of the needle was apparent on the other side of the cylinder. The assembly was similar to the depictions of FIG. 4A and FIG. 4B and was stored until use.

A cartridge filled with deep blue shade solution was inserted in an automatic pen injector (Autopen). The 31 gauge pen-needle was affixed to the automatic pen injector which was subsequently purged of residual air. The injection volume was set to 0.05 mL.

The device was positioned on an enucleated albino rabbit eye. To do so, the slidable platform was positioned on the pars plana area of the eye by positioning of the edge of the slidable platform at the limbus. Following positioning of the movable platform on the pars plana area, the device was pushed toward the eye which resulted in the fixed needle penetrating inside the eye tissue while the slidable platform was allowed to slide alongside the shaft of the needle until it was stopped by the fixed platform. Injection of 0.05 mL was subsequently achieved by pressing the actuation button of the automatic pen injector and the device was subsequently pulled out of the eye. These steps are illustrated in FIG. 5B through FIG. 5D. The experiment was repeated in 3 additional enucleated rabbit eyes using identical devices.

Following the experiment, observation of the eyes demonstrated successful intravitreal injections as evidenced by the blue color visible from the corneal side of the eyes. Subsequent dissection confirmed the observation. Minimal contamination of the conjunctiva at the pars plana area was also noted.

This example confirmed the usefulness of the invention using an automatic pen injector equipped with a slidable platform for precise and easy application to the pars plana area and injection of drug substances into the vitreous.

Example 3

A compressible platform having a diameter of 6 mm and a thickness of 9 mm was cut out from a sheet made of flexible reticulated polyurethane cell foam. The platform was pieced in its center by a 31 gauge pen-needle until the tip of the needle was apparent on the other side of the cylinder. The assembly was similar to the depictions of FIG. 6A and FIG. 6B and was stored until use.

A cartridge filled with deep blue shade solution was inserted in an automatic pen injector (Autopen). The 31 gauge pen-needle was affixed to the Autopen which was subsequently purged of residual air. The injection volume was set to 0.05 mL.

The device was positioned on an enucleated albino rabbit eye. To do so, the slidable platform was positioned on the pars plana area of the eye by positioning of the edge of the slidable platform at the limbus. Following positioning of the compressible platform on the pars plana area, the device was pushed toward the eye which resulted in the fixed needle penetrating inside the eye tissue until penetration was stopped by complete compression of the compressible platform. Injection of 0.05 mL was subsequently achieved by pressing the actuation button of the Autopen and the device was subsequently pulled out of the eye. These steps are illustrated in FIG. 7B through FIG. 7D. The experiment was repeated in 3 additional enucleated rabbit eyes using identical devices.

Following the experiment, observation of the eyes demonstrated successful intravitreal injections as evidenced by the blue color visible from the corneal side of the eyes. Subsequent dissection confirmed the observation. Minimal contamination of the conjunctiva at the pars plana area was also noted.

This example confirmed the usefulness of the invention using an automatic pen injector equipped with a compressible platform for precise and easy application to the pars plana area and injection of drug substances into the vitreous.

As will readily be appreciated by one having ordinary skill in the art, the present invention provides numerous advantages compared to prior art methods and systems for administering agents and formulations thereof to the eye. Among the advantages are the following:

The provision of an intravitreal injection method and system that provides safe, accurate, consistent, and rapid injection of therapeutic agents into the intravitreal compartment of the eye.

The provision of an intravitreal injection method and system that facilitates injection of therapeutic agents into the intravitreal compartment of the eye with minimal risk of trauma to the patients' eye by the delivery device.

The provision of an intravitreal injection method and system that provides semiautomated injection of therapeutic agents into the intravitreal compartment of the eye.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An intravitreal injection device, comprising:
   an injection member having a formulation chamber, a needle and a transitional guide platform, said formulation chamber being adapted to receive and contain a pharmacological agent formulation therein, said needle having a first end that is in communication with said formulation chamber and a second ejection end, said transitional guide platform comprising a compressible guide platform, said compressible guide platform comprising a non-reticulated closed-cell foam having a predetermined degree of flexibility, whereby said transitional guide platform substantially conforms to the surface of a sclera of an eye when in an engagement position thereon.

2. An intravitreal injection device, comprising:
   an injection member having a formulation chamber, a needle and a transitional guide platform, said formulation chamber being adapted to receive and contain a pharmacological agent formulation therein, said needle having a first end that is in communication with said formulation chamber and a second ejection end, said transitional guide platform comprising a compressible guide platform, said compressible guide platform comprising a reticulated open-cell foam having a predetermined degree of flexibility, whereby said transitional guide platform substantially conforms to the surface of a sclera of an eye when in an engagement position thereon.

3. An intravitreal injection device, comprising:
   an injection member having a formulation chamber, a needle and a transitional guide platform, said formulation chamber being adapted to receive and contain a pharmacological agent formulation therein, said needle having a first end that is in communication with said formulation chamber and a second ejection end, said transitional guide platform comprising a compressible guide platform, said compressible guide platform comprising a reticulated open-cell foam, said reticulated open-cell foam comprising a polymeric material selected from the group consisting of polyvinylchloride, polyurethane, polystyrene, polypropylene, polyethylene, crosslinked polyethylene, ethyl vinyl acetate, polyesters, vinyl nitrile neoprene and mixtures thereof, said compressible guide platform having a predetermined degree of flexibility, whereby said transitional guide platform substantially conforms to the surface of a sclera of an eye when in an engagement position thereon.

* * * * *